United States Patent [19]

Johnson et al.

[11] 4,322,522

[45] Mar. 30, 1982

[54] POLYESTER/POLYETHER SEGMENTED COPOLYMERS STABILIZED AGAINST DEGRADATION BY U.V. LIGHT VIA COPOLYMERIZATION WITH ANALOGS OF 2,2,6,6-TETRAMETHYLPIPERIDINE DERIVATIVES

[75] Inventors: David A. Johnson, Norton, Mass.; Robert C. Gilly; Kenneth B. Wagener, both of Asheville, N.C.

[73] Assignee: Akzona Incorporated, Asheville, N.C.

[21] Appl. No.: 164,043

[22] Filed: Jul. 8, 1980

[51] Int. Cl.$^3$ .................... C07D 487/10; C08G 63/16
[52] U.S. Cl. .................................... 528/289; 546/20
[58] Field of Search ..................... 528/289; 546/20

[56] References Cited

U.S. PATENT DOCUMENTS

| | | |
|---|---|---|
| 3,480,635 | 11/1969 | Altwicker . |
| 3,536,722 | 10/1970 | Murayama et al. . |
| 3,542,729 | 11/1970 | Murayama et al. . |
| 3,640,928 | 2/1972 | Murayama et al. . |
| 3,684,765 | 8/1972 | Matsui et al. . |
| 3,705,126 | 12/1972 | Matsui et al. . |
| 3,705,166 | 12/1972 | Murayama et al. . |
| 3,828,052 | 8/1974 | Holt et al. . |
| 3,850,877 | 11/1974 | Cook . |
| 3,901,853 | 8/1975 | Tanikella .............................. 528/289 |
| 3,904,581 | 9/1975 | Murayama et al. . |
| 3,910,860 | 10/1975 | Tanikella . |
| 3,937,711 | 2/1976 | Cook . |
| 3,939,168 | 2/1976 | Cook . |
| 3,940,363 | 2/1976 | Murayama et al. . |
| 3,956,294 | 5/1976 | Eleckenstein et al. . |
| 3,970,636 | 7/1976 | Hardy et al. . |
| 3,971,795 | 7/1976 | Cook . |
| 3,974,127 | 8/1976 | Tanikella et al. . |
| 4,001,189 | 1/1977 | Tanikella et al. . |
| 4,001,190 | 1/1977 | Tanikella et al. . |
| 4,005,094 | 1/1977 | Murayama et al. .................. 546/20 |
| 4,021,432 | 5/1977 | Holt et al. . |
| 4,038,280 | 7/1977 | Randell et al. . |
| 4,046,736 | 9/1977 | Hardy . |
| 4,051,616 | 12/1977 | Murayama et al. . |
| 4,055,563 | 10/1977 | Soma et al. ......................... 260/8 N |
| 4,056,507 | 11/1977 | Ramey et al. . |
| 4,102,867 | 7/1978 | Ponton, Jr. et al. ................. 528/289 |
| 4,113,704 | 9/1978 | MacLean et al. ................... 528/289 |
| 4,136,090 | 1/1979 | Hoeschele ........................... 528/289 |

FOREIGN PATENT DOCUMENTS

| | | |
|---|---|---|
| 1016292 | 8/1977 | Canada . |
| 47-79798 | 8/1972 | Japan . |
| 47-331950 | 11/1972 | Japan . |
| 48-39038 | 11/1973 | Japan . |
| 48-39039 | 11/1973 | Japan . |
| 50-91652 | 4/1976 | Japan . |

Primary Examiner—John Kight, III
Assistant Examiner—R. A. White
Attorney, Agent, or Firm—Francis W. Young; Jack H. Hall; H. Walter Haeussler

[57] ABSTRACT

Polyester/polyether segmented copolymers are stabilized against degradation by UV light via copolymerization with novel diesters and/or bis-hydroxyalkyl terminated derivatives of 2,2,6,6-tetramethylpiperidines.

7 Claims, No Drawings

POLYESTER/POLYETHER SEGMENTED COPOLYMERS STABILIZED AGAINST DEGRADATION BY UV LIGHT VIA COPOLYMERIZATION WITH ANALOGS OF 2,2,6,6-TETRAMETHYLPIPERIDINE DERIVATIVES

BACKGROUND OF THE INVENTION

Polyester polyether segmented copolymers can be widely utilized in the synthetic polymer art in various shapes or forms, for example, filament, fiber, yarn, film, sheet, or other molded articles. However, these polymers have a draw-back in that they possess poor ultraviolet light stability, that is, they undergo severe deterioration when exposed to light such as sunlight or ultraviolet light. For the purposes of stabilizing these polymers against such deterioration, there have heretofore been proposed in the art a number of stabilizers, for example, such as phenols, amines, compounds containing both hydroxyl and amine groups and salts of multivalent metals. Although such stabilizers are considered as satisfactory for some polymer applications, attempts have been made to develop new and more effective stabilizers.

It has been found that the copolymerization of novel 2,2,6,6-tetramethypiperidine derivative monomers of the present invention into the backbone of the polyester/polyether segmented copolymer produces a polymer which has much improved stability against the degradating effects of ultraviolet light, as well as good processability characteristics.

SUMMARY OF THE INVENTION

According to the present invention, polyester/polyether segmented copolymers are stabilized against degradation by ultraviolet light, hereinafter UV light, via copolymerization with novel 2,2,6,6-tetramethylpiperidine derivatives.

The novel 2,2,6,6-tetramethylpiperidine derivatives which are copolymerized with polyester/polyether copolymers function as stabilizers against degradation by UV light in the present invention and are represented by structural formulas I and II:

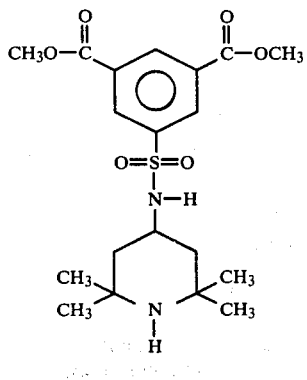

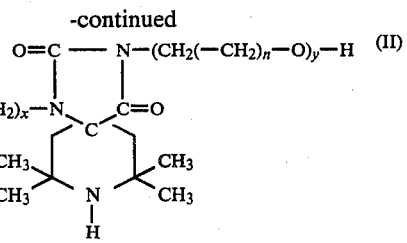

Wherein the sum of x plus y is within the range of 2 to 30, preferably 2 to 12 and n is an integer from 1 to 4.

The introduction of either or both of the 2,2,6,6-tetramethylpiperidine derivatives of formulas I and II into the backbone of polyester/polyether copolymer chain increases the photostability of the copolymerized product and increases the durability of these stabilizers toward further processing, such as dyeing and finishing, and toward normal use operations such as washing. Copolymerization also minimizes any toxological effects which might arise from the use of the piperidine derived stabilizer additives.

The polyester/polyether segmented copolymers which are stabilized in the present invention are disclosed in copending application, Ser. No. 752,587, filed Dec. 20, 1978, which is hereby incorporated by reference, and consist essentially of a multiplicity of randomly occuring intrachain segments of long-chain (soft segments) and short-chain (hard segments) ester units, the long-chain ester units being represented by the following structure:

where L is a divalent radical remaining after removal of terminal hydroxyl groups from poly (oxyalkylene) glycols having at least 1 nitrogen containing ring per molecule, a carbon to nitrogen ration of from about 3/1 to about 350/1, and a molecular weight between 200 and 8,000, and R is a divalent radical remaining after the removal of the carboxyl groups from a dicarboxylic acid having a molecular weight of less than 300.

Short-chain ester units are represented by the following structure:

where E is a divalent radical remaining after removal of hydroxyl groups from a low molecular weight diol having 2 to 15 carbon atoms per molecule and a molecular weight between 50 and 250, and R is the divalent radical described for (II) above.

The introduction of a foreign repeat unit in the backbone of a crystallizable soft segment, such as a polyether, has an effect on the soft segment crystallization process. Such a foreign unit must be stable to processing temperatures and must not be so rigid as to reduce the mobility (raise the glass transition temperature) of the soft segment itself. The foreign unit should be non-reactive during the synthesis of the segmented thermoplastic elastomer and should be present in the concentration of at least 1 unit per polyether molecule of the long-chain ester.

The polyether soft segment of the present invention may be represented by the following structures:

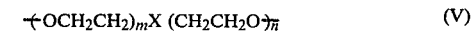

or

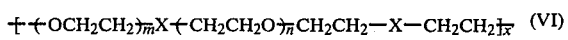

In (V), the unit X is placed near the center of the polyether chain and may be one foreign unit or a series of foreign units covalently linked together. In (VI), the unit X is one or more foreign repeat units as in (V) but these units are placed along the length of the linear polyether chain.

In both formulas (V) and (VI), X is a nitrogen containing heterocyclic ring giving the polyether soft segment a carbon to nitrogen ratio of from about 3/1 to about 350/1 and a molecular weight between 200 and 8,000. The sum of m plus n is within the range of 5 to 20, and x' in formula (VI) has a maximum value of 10.

The nature of X is such that it may covalently enter the polyether chain to influence crystallization. Covalent links to the polyether in (V) or (VI) may be an amide link or the imide link, both of which are capable of withstanding high temperature processing. These links, the polyester units themselves, and the foreign unit(s) X in (V) or (VI) form the soft segment.

The introduction of the repeat unit X into the poly-(oxyethylene) chain, where X is greatly different from poly (oxyethylene), disrupts chain regularity and suppresses the melting point of the soft segment preventing crystallization at room temperature. This allows the use of higher molecular weight polyethers, or stated differently, lower percentage of the soft segment. The lower mole percentage of soft segment increases the melting point of the copolymer due to higher mole percentage of the hard segment. Also a more regular chain is obtained which may result in better separation of the hard and soft phases. Better phase separation results in a high tenacity, a lower glass transition temperature for the soft segment, and an improved elastomeric performance.

The novel 2,2,6,6-tetramethylpiperidine derivatives of formulas I and II can be added to the reaction of formation of the polyester/polyether copolymer at the beginning of the ester interchange (transesterification) or at any stage of polycondensation. Their addition can be accomplished without any deterioration of polymer color or any loss of intrisic viscosity which implies that these derivatives possess the thermal stability for high temperature processing which is uncharacteristic of UV stabilizers.

While the monomer of formula I can be incorporated into either the lone-chain or the short-chain polyester units, the monomer of formula II is incorporated into the long-chain polyester units of the polyester/polyether segmented copolymer, thus, it places the UV stabilizing piperidine unit in the approximate center of a soft segment, which in itself guarantees the proximity of the stabilizing moiety to the initial site of UV degradation.

DETAILED DESCRIPTION OF THE INVENTION

Polyester/polyether segmented copolymers are stabilized against degradation by UV light via copolymerization with diesters and/or bis-hydroxy alkyl terminated derivatives of 2,2,6,6-tetramethylpiperidines.

THE STABILIZER MONOMERS

The 2,2,6,6-tetramethylpiperidine derivatives which can be copolymerized with the polyester/polyether copolymers are represented by structural formulas I and II.

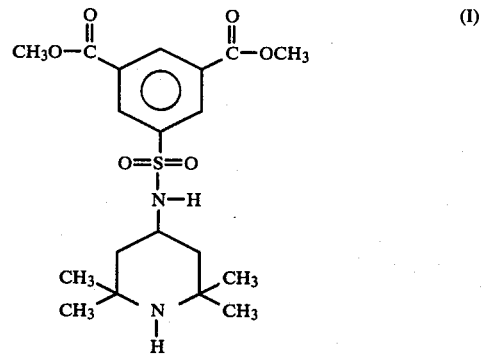

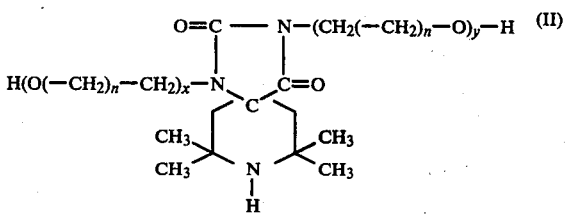

wherein the sum of x plus y is within the range of 2 to 30, preferrably 15 to 25 and n is an integer from 1 to 4.

The stabilizer compound of structural formula I is N-[2,2,6,6-tetramethyl-4-piperidyl]-3,5-dicarboxymethylbenzene sulfonamide. This compound copolymerizes with the components of the polyester/polyether copolymer at the beginning of ester interchange or at any stage of polycondensation.

The stabilizer compound of formula I copolymerizes with the components of the polyester/polyether copolymer by transesterification. The two terminal methoxy groups on the compound of formula I undergo transesterification with terminal hydroxy groups of any hydroxy groups containing component in use during the formulation of the polyester/polyether copolymer to produce free methanol and divalent radical of the formula:

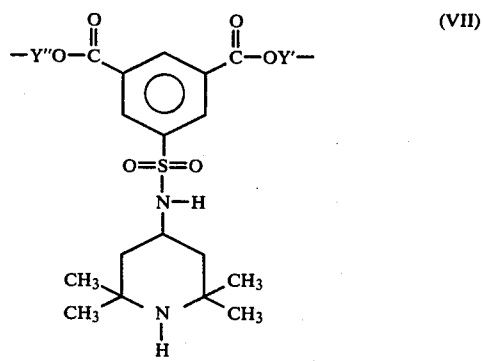

wherein Y' and Y" each represent a monovalent substituent in the polyester/polyether copolymer. Thus, through transesterification, the stabilizer compound of formula I can be incorporated into either the long-chain or the short-chain ester units of the polyester/polyether segmented copolymer as a replacement for any dicarboxylic acid in use in the long-chain or short-chain ester unit formulation.

The stabilizer compounds of formula II which are covalently bonded into the soft segment chain of the polyester/polyether segmented copolymer are generically named 2,2,6,6-tetramethylpiperidine-4-spiro-[1,3-bis-poly (alkoxy) hydantoin glycol].

In formula II the sum of x plus y ranges from 2 to 30, preferably from 15 to 25 and n is an integer from 1 to 4. Illustrative examples of stabilizers of formula II which are useful in producing the stabilized polyester/polyether copolymers of the present invention include:
2,2,6,6-tetramethylpiperidine-4-spiro-[1,3-bis-(ethoxy) hydantoin glycol],
2,2,6,6-tetramethylpiperidine-4-spiro-[1,3-bis-(diethoxy) hydantoin glycol],
2,2,6,6-tetramethylpiperidine-4-spiro-[1,3-bis-(tetraethoxy) hydantoin glycol],
2,2,6,6-tetramethylpiperidine-4-spiro-[1,3-bis-(hexaethoxy) hydantoin glycol],
2,2,6,6-tetramethylpiperidine-4-spiro-[1,3-bis-(dimethoxy) hydantoin glycol],
2,2,6,6-tetramethylpiperidine-4-spiro-[1,3-bis-(tripropoxy) hydantoin glycol],
2,2,6,6-tetramethylpiperidine-4-spiro-[1,3-bis-(dibutoxy) hydantoin glycol]

The preferred stabilizing monomers are 2,2,6,6-tetramethylpiperidine-4-spiro [1,3-bis-poly(ethoxy) hydantoin glycol] compounds containing a total of from 2 to 12 ethoxy groups.

The 2,2,6,6-tetramethylpiperidine-4-spiro-[1,3-bis-poly (alkoxy) hydantoin glycol] stabilizer compounds of formula II are incorporated solely into the long-chain ester units of the polyester/polyether segmented copolymers. These stabilizer compounds are reacted with dicarboxylic acids or their derivatives which will be discussed under the subject matter heading "Other Polyester/Polyether Segmented Copolymer Components".

About 0.01 to 5.0 weight percent, preferably 0.2 to 2.0 weight percent of one or more of stabilizer components as represented by formulas I and II is copolymerized with bis-hydroxy terminated ester-comonomers and ether prepolymers to form the UV stabilized polyester/polyether segmented copolymers of the present invention. The copolymerization of the preferred amount of stabilizer results in an eight-fold improvement in photostability as compared to non-stabilized untreated polyester/polyether copolymers.

OTHER POLYESTER/POLYETHER SEGMENTED COPOLYMER COMPONENTS

The term "foreign repeat unit" as applied to the soft segments of this invention refers to heterocyclic, nitrogen containing, rings which may covalently link (as amide or imide) along the soft segment chain as described previously. Representative units are: 1,3-divalent-5,5-dialkylhydantoin (including alkyl groups connected in a cyclic fashion to the 5,5 positions): 2,5-divalent-1,3,4-triazole; 2,5-divalent-1,3,4-oxadizaole; 2,-divalent-1,3,4-thiadiazole; 1,3-divalent-1,2,4-triazolidine-3,5-done; 4,5-divalent-1,2-isothiazole; 4,5-divalent-1,2-oxazole; 4,5-divalent-1,3-diazole; 2,5-divalent-1,3-oxazole; 2,4-divalent-imidazole; divalent (N position) hypoxanthine; and 2,5-divalent-1,3-thiazole.

The term "long-chain ester units" as applied to units in the copolymer chain refers to the reaction product of a long-chain glycol with a dicarboxylic acid. Such "long-chain ester units", which are repeating units in the copolyesters of this invention, correspond to formula (III) above. The long-chain glycols are polymeric glycols having terminal hydroxy groups and a molecular weight above about 400 and perferrably about 1,000 to 3,000. The long-chain glycol used to prepare the copolyesters of this invention are poly(oxyalkylene) glycols having foreign repeat units represented by formulas VII and VIII:

$$H(OCH_2CH_2)_mX (CH_2CH_2O)_nH \tag{VII}$$

$$H[(OCH_2CH_2)_mX(CH_2CH_2O)_nCH_2CH_2-X-CH_2CH_2]_{x'}OH \tag{VIII}$$

The poly(oxyalkylene) glycols have carbon to nitrogen ratios between about 3/1 and about 350/1, molecular weights between 200 and 8,000, m plus n is with the range of 5 to 20, and x' in formula (VIII) has a maximum value of 10. In a preferred embodiment, the poly (oxyalkylene) glycols have carbon to nitrogen ratios between about 8.5/1 and about 23/1 and molecular weights between 450 and 8,000. Representative long-chain glycols are poly (oxyethylene) glycol, poly (oxypropylene) glycol, poly (oxymethylethylene) glycol, poly (oxytetramethylene) glycol, and random copolymers of ethylene oxide and 1,2-propylene oxide.

The term "short-chain ester units" as applied to units in the copolymer chain refers to low molecular weight compounds for polymer chain units having molecular weights less than about 500. They are made by reacting a low molecular weight diol (below about 250) with a dicarboxylic acid to form ester units represented by formula (IV) above.

Included among the low molecular weight diols which react to form the short-chain ester units are acyclic, alicyclic, and aromatic dihydroxy compounds. Preferred are diols with 2 to 15 carbon atoms such as ethylene, propylene, 1,4-butane, pentamethylene, 2,2-dimethyl trimethylene, hexamethylene, and decamethylene, glycol; dihydroxycyclohexane; cyclohexane dimethanol, resorcinol; hydroquinone; 1,5-dihydroxy naphthaline, etc. Especially, preferred are aliphatic diols containing 2 to 8 carbon atoms. Equivalent ester-forming derivatives of diols are also useful (e.g. ethylene oxide or ethylene carbonate can be used in place of ethylene glycol). The term "low molecular weight diols" as used herein should be construed to include such equivalent ester-forming derivatives; provided however, that the molecular weight requirement pertains to diol only and not to its derivatives.

Dicarboxylic acids which are reacted with the foregoing long-chain glycols (L in formula III) and low molecular weight diols (E in formula IV) to produce the copolyesters of this invention are aliphatic, cycloaliphatic, or aromatic dicarboxylic acids of a low molecular weight, i.e., having a molecular weight of less than about 300. The term "dicarboxylic acids" as used herein, includes equivalents of carboxylic acids having 2 functional carboxyl groups which perform substantially like dicarboxylic acids in reaction with glycols and diols in forming copolyester polymers. These equivalents include esters and esterforming derivative.

Thus, an ester of a dicarboxylic acid having a molecular weight greater than 300 or an acid equivalent of a dicarboxylic acid having a molecular wight greater than 300 are included provided the corresponding acid has a molecular weight below about 300. The dicarboxylic acids can contain any substituent groups or combinations which do not substantially interfere with the copolyester polymer formation and use of the polymer of this invention.

Aliphatic dicarboxylic acids, as the term is used herein, refers to the carboxylic acids having 2 carboxyl groups each attached to a saturated carbon atom. If the carbon atom to which the carboxylic acid groups is attached is saturated and is in a ring, the acid is cycloaliphatic. Aliphatic or cycloaliphatic acids having conjugated unsaturation often can be used provided they are thermally stable at polymerization temperatures and do not undergo homopolymerization.

Aromatic dicarboxylic acids, as the term is used herein, are dicarboxylic acids having 2 carboxyl groups attached to a carbon atom in a isolated or fused benzene ring. It is not necessary that both functional carboxyl groups be attached to the same aromatic ring and where more than 1 ring is present, they can be joined by aliphatic or aromatic divalent radicals or divalent radicals such as —O— or —SO$_2$—.

Representative aliphatic and cycloaliphatic acids which can be used for this invention are sebasic acid, 1,3-cyclohexane dicarboxylic acid, 1,4-cyclohexane dicarboxylic acid, adipic acid, glutaric acid, succinic acid, carbonic acid, oxalic acid, azelaic acid, dimethylmalonic acid, allylmalonic acid, 4-cyclohexene-1,2-dicarboxylic acid, 2-ethyl suberic acid, 2,2,3,3-tetramethyl succinic acid, cyclopentane dicarboxylic acid, decahydro-1,5-naphthalene dicarboxylic acid, 4,4-bicyclohexyl dicarboxylic acid, decahydro-2,6-naphthalene dicarboxylic acid, 4,4-methylene bis-(cyclohexane carboxylic acid), 3,4-furan dicarboxylic acid, and 1,1-cyclobutane dicarboxylic acid. Preferred aliphatic acids are cyclohexane dicarboxylic acids and adipic acid.

Representative aromatic dicarboxylic acids which can be used include terephthalic, phtalic and isophthalic acids, dibenzoic acid, substituted dicarboxylic acids with two benzene nuclei such as bis (p-carboxyphenyl) methane, p-oxy (p-carboxy-phenyl) benzoic acid, ethylene-bis (p-oxybenzoic acid), 1,5-naphthalene dicarboxylic acid, 2,6-naphthalene dicarboxylic acid, 2,7-naphthalene dicarboxylic acid, phenanthrene dicarboxylic acid, anthrancene dicarboxylic acid, 4,4'-sulfonyl dibenzoic acid, and $C_1$-$C_{12}$alkyl and ring substitution derivatives thereof, such as halo, alkoxy, and aryl derivatives. Hydroxy acids such as (p-hydroxy ethoxy) benzoic acid can also be used provided an aromatic dicarboxylic acid is also present.

Aromatic dicarboxylic acids are a preferred class for preparing the copolester polymers of this invention. Among the aromatic acids, thos with 8 to 16 carbon atoms are preferred, particularly the phenylene dicarboxylic acids, i.e., terephthalic, phthalic and isphthalic acids.

Polymers described herein can be made conveniently by a conventional ester interchange reaction such as that described in detail to U.S. Pat. NO. 2,763,109. Other special polymerization techniques, for example interfacial polymerization, may prove useful for preparation of specific polymers. Both batch and continuous methods may be used for any stage of copolyester polymer preparation. Polycondensation of prepolymers can alos be accomplished in the solid prepolymer in a vacuum or in a stream of inert gas to remove liberated low molecular weight diol. This method has the advantage of reducing degradation because it must be used at temperatures below the softening point of the prepolymer.

The 2,2,6,6-tetramethylpiperidine derivatives of formulas I and II can be added to the reaction of formation of the polyester/polyether segmented copolymer at the beginning of ester interchange or at any stage of polycondensation. Optionally, catalysts such as tetrabutyltitenate can be employed in the reaction mix to promote polymerization.

By the incorporation of one or more of the stabilizing monomers into the polyester/polyether copolymers, the copolymers of the present invention are stabilized against ultraviolet radiation. Additional stabilizers may be added to the copolymer in addition to the stabilizing monomers. Satisfactory stabilizers comprise phenols and their derivatives, amines and their derivatives, compounds containing both hydroxyl and amine groups, hydroxyazine, oximes, polymeric phenolic esters and salts of multivalent metals in which the metal is in its lower valent state.

The properties of these copolyesters can be modified by the incorporation of various conventional inorganic compounds such as titanium dioxide, carbon black, silica gel, alumina, clays, and chopped fiber glass.

All parts, proportions, and percentages disclosed herein are by weight unless otherwise indicated. The following examples further illustrate the invention.

EXAMPLE IA

PREPARATION OF N-[2,2,6,6-TETRAMETHYL-4-PIPERIDYL]-3,5-DICARBOXYMETYHYLBENZENE SULFONAMIDE

In a 50 ml three neck round bottom flask was placed 10 g of 4-amino-2,2,6,6-tetramethylpiperidine in 20 ml of dry methylene chloride. The reaction flask was then equipped with a small magnetic stirring bar and reflux condenser. A 100 ml additional funnel, containing 18.6 g of 3,5-dicarboxymethylbenzene sulfonyl chloride in 10 ml of methylene chloride, was placed on the reaction flask. The reaction vessel was purged with dry nitrogen and an addition of sulfonyl chloride was completed in 1 hour. The reaction mixture was allowed to stir overnight at room temperature, after which the white solid precipitate was neutralized with 25% sodium methoxide in methanol (10.1 ml, 0.6399 mole), vacuum filtered and dried in a vacuum overnight at 125° C., yielding 22 g, 83% yield, M.P. 220° C., of N-[2,2,6,6-tetramethyl-4-piperidyl]-3,5-dicarboxymethylbenzene sulfonamide.

EXAMPLE IB

SYNTHESIS OF HYDANTION POLYETHER/POLY(BUTYLENE TEREPHTHALATE) SEGMENTED COPOLYMER CONTAINING N-[2,2,6,6-TETRAMETHYL-4-PIPERIDYL]-3,5-DICARBOXYMETHYLBENZENE SULFONAMIDE

On one kg. resin kettle is charged with 200 g. (1.03 moles) dimethyl terephthalate, 126 g. (1.4 moles) 1,4-Butanediol, 219 g. (0.219 moles) hydantoin polyether prepolymer having an average molecular weight of approximately 1,000 (Dantocol DHE-20 Glycol Inc.), 4.46 g (1.06 wt.% antioxidant 330 (Ethyl Corporation), and 4.46 g. (1.06 wt%) N-[2,2,6,6-tetramethyl-4-piperidyl]-3,5-dicarboxymethylbenzene sulfonamide. The resin kettle is equipped with a mechanical stirrer, a nitrogen inlet tube, a thermocouple connected to a Barber-Coleman recorder and a dual partial condenser of which the lower column is heated to 130° C. by a circulating oil bath and the upper column is heated to 70° C. by a circulating hot water bath. The condenser is mounted above an automatic liquid dividing distillation head.

The system is continuously purged with nitrogen and is heated using a heating mantle to 120° C. where low speed stirring is started. When the temperature of the reaction mix reaches 125° C., 202 mg. tetrabutyltitante catalyst (approximately 0.10 wt.% based on dimethyl terephthalate) is added in 10 ml hexane. The ester interchange reaction begins at 175°-185° C. as 100 percent of the theoretical amount of methanol is distilled. The ester interchange product is poured quickly into a one kg. polymerization kettle and cooled under a nitrogen blanket to room temperature. The polymerization is started using a Dowtherm boiler to melt the ester interchange product and upon the completion of melting a vacuum cycle is started in which the vacuum is maintained for 85 minutes below 0.1 mm. A hydantoin polyether poly (butylene terephthalate) segmented copolymer containing N-[2,2,6,6-tetramethyl-4-piperidyl]-1,3-dicarboxymethylbenzene sulfonamide linkages is produced. The polymer is extruded into tap water at 40° C. and has an intrinsic viscosity of 1.2 to 1.3 in a solvent consisting of 60 parts phenol/40 parts tetrachloroethane at 25° C., a $T_m$ of 165°-180° C., an elongation of 400 to 500% and an initial modulus of 0.8 g./d. The product polymer shows no appreciable change of polymer color as compared to unstabilized hydantoin polyether poly (butylene terephthalate) comonomer hereinafter referred to as the original or control polymer.

EXAMPLE IC

The product polymer of Example IB was ground, vacuum dried, and spun using a ½ inch extruder into 100/13 undrawn yarn. This yarn, along with control yarn similarly produced from the control polymer, was wound into skeins and exposed up to 100 hours in a fluorescent light box (black light). Samples were taken at 5-hour intervals through 20 hours and at 20-hour intervals through 100 hours. Strength retention data was determined by Anstron testing the original as well as the exposed yarn. Results of these tests are listed in Table I.

TABLE I

| STRENGTH RETENTION DATA FOR FIBERS | | | | |
|---|---|---|---|---|
| Exposure Time, Hrs. | Denier | Breaking Strength (gms) | Tenacity g/d | Strength Retention (%) |
| Stabilized Yarn[a] (Original) | | | | |
| 0 | 97 | 68.6 | 0.84 | 100 |
| 5 | | 55.5 | 0.56 | 80 |
| 10 | | 46.7 | 0.48 | 69 |
| 15 | | 30.4 | 0.31 | 45 |
| 20 | | 30.4 | 0.31 | 45 |
| 40 | | 6.3 | 0.06 | 9 |
| 60–100 | | 0.0 | 0.0 | 0 |
| Unstabilized (Control) Yarn[b] (Original) | | | | |
| 0 | 107 | 77.1 | 0.71 | 100 |
| 5 | | 42.2 | 0.39 | 55 |

TABLE I-continued

| STRENGTH RETENTION DATA FOR FIBERS | | | | |
|---|---|---|---|---|
| Exposure Time, Hrs. | Denier | Breaking Strength (gms) | Tenacity g/d | Strength Retention (%) |
| 10–100 | | 0.0 | 0.0 | 0 |

[a] 97 denier undrawn PBT/HPOE-1000, 50:50 wt % elastomer containing 1.0 wt % antioxidant 330 and 1.0 wt % N-[2,2,6,6-tetramethyl-4-piperidyl]-1,3-dicarboxymethylbenzene sulfonamide (as prepared in Example IB).
[b] 107 denier undrawn PBT/HPOE-1000, 50:50 wt % elastomer containing 1.0 wt % antioxidant 330 (control).

EXAMPLE ID

The product polymer as produced in Example IB was dissolved in chloroform, precipitated in hexane, then cast into 5 mil thick films from chloroform. These films were exposed up to 20 hours in a fluorescent box along with films prepared in an identical manner from the control polymer (no UV stabilizer comonomer present). Results of these tests are given in Table II.

TABLE II

| STRENGTH RETENTION DATA FOR 5 MIL FILMS | | |
|---|---|---|
| Exposure Time, Hrs. | Breaking Strength lb/in² | Strength Retention, % |
| Stabilized Film² (Original) | | |
| 0 | 2207 | 100 |
| 5 | 2091 | 95 |
| 10 | 1832 | 83 |
| 15 | 1775 | 80 |
| 20 | 1555 | 70 |
| Unstabilized (Control) Film | | |
| 0 | 2471 | 100 |
| 5 | 1198 | 42 |
| 10–20 | 0 | 0 |

EXAMPLE IIA

SYNTHESIS OF 2,2,6,6-TETRAMETHYLPIPERIDINE-4-SPIRO-[1,3-BIS-POLY(ALKOXY)-HYDANTOIN GLYCOL]

A 250 ml round bottom flask was charged with a solution of 20 g. of 2,2,6,6-tetramethyl-4-piperidine hydrochloride in 50% ethanol, 40 g. ammonium carbonate and 8.5 g. potassium cyanide. The reaction mixture is heated and stirred for 16 hours within a temperature range of 50°-80° C. The reaction mixture is cooled below room temperature to produce a precipitate which is filtered and washed with water. This product is recrystallized from dilute ethanol to yield 26 g. of 2,2,6,6-tetramethyl-piperidine-4-spiro-5-hyantoin product. This product is alkoxylated in the following manner using any of a variety of alkylene oxides such as ethylene oxide.

A 50 ml. flask equipped with a stirrer, gas inlet and outlet tubes is charged with 1 mole of 2,2,6,6-tetramethylpiperidine-4-spiro-5-hydantoin product and heated to 200° C. with vigorous stirring. Two moles of ethylene oxide is added to produce 2,2,6,6-tetramethylpiperidine-4-spiro-[1,3-bis-ethoxy hydantoin glycol]. Polyethoxy derivatives can be produced by continuing the addition of ethylene oxide until the desired degree of ethoxylation is reached.

The UV stabilized polyester/polyether copolymers containing 2,2,6,6-tetramethypiperidine-4-spiro-[1,3-bis-poly(alkoxy) hydantoin glycol] linkages can be prepared using the method of Example IB wherein 2,2,6,6-tetramethylpiperidine-4-spiro-[1,3-bis-poly(alkoxy) hydantoin glycol]monomer replaces all or a portion of the N-[2,2,6,6-tetramethyl-4-piperidyl]-3,5-dicarboxymethylbenzene sulfonamide as the difunctional monomer.

We claim:

1. A polyester/polyether segmented copolymer stabilized against deterioration caused by ultraviolet light by the copolymerization into the copolymer of a stabilizing amount of one or more stabilizing comonomers selected from the group consisting of:

compounds having a formula

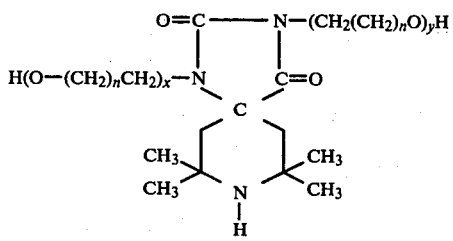

wherein n is an integer from 1 to 4 and the sum of x plus y ranges from 2 to 30.

2. The copolymer as claimed in claim 1 wherein the stabilizing amount of said stabilizing comonomers is 0.01 to 5.0 weight percent of the copolymer.

3. The copolymer as claimed in claim 2 wherein the stabilizing amount of said stabilizing comonomers is 0.2 to 2 weight percent of the copolymer.

4. The copolymer as claimed in claim 1 wherein n is 1 and the sum of x plus y ranges from 2 to 12.

5. A 2,2,6,6-tetramethypiperidine compound having the formula:

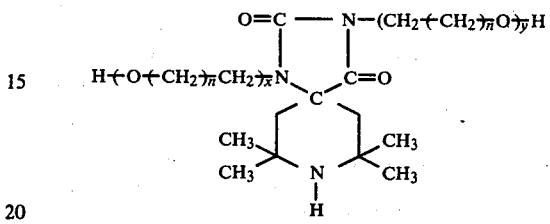

wherein n is an integer from 1 to 4 and the sum of x plus y ranges from 2 to 30.

6. The compound as defined in claim 5 wherein n is 1 and the sum of x plus y ranges from 15 to 25.

7. N-2,2,6,6-tetramethylpiperidine-4-spiro-[1,3-bis-poly(alkoxy) hydantoin glycol].

* * * * *

UNITED STATES PATENT AND TRADEMARK OFFICE
CERTIFICATE OF CORRECTION

PATENT NO. : 4,322,522

DATED : March 30, 1982

INVENTOR(S) : David A. Johnson, Robert L. Lilly, Kenneth B. Wagener

It is certified that error appears in the above—identified patent and that said Letters Patent is hereby corrected as shown below:

On the title page, Item [75]:

Please correct the name of the second inventor from Robert C. Gilly to Robert L. Lilly.

In Claim 5, line 1 correct the spelling of "2,2,6,6-tetramethylpiperidine".

In Claim 7, line 1 delete "N-".

Signed and Sealed this

Fifteenth Day of June 1982

[SEAL]

Attest:

Attesting Officer

GERALD J. MOSSINGHOFF

Commissioner of Patents and Trademarks